US005266500A

United States Patent [19]

Scensny et al.

[11] Patent Number: 5,266,500

[45] Date of Patent: Nov. 30, 1993

[54] ATTACHMENT OF COMPOUNDS TO POLYMERIC PARTICLES USING DICATION ETHERS AND A KIT CONTAINING SAME

[75] Inventors: Patricia M. Scensny; Chung-yuan Chen, both of Rochester, N.Y.

[73] Assignee: Eastman Kodak Company, Rochester, N.Y.

[21] Appl. No.: 389,390

[22] Filed: Aug. 3, 1989

[51] Int. Cl.$^5$ .......... G01N 33/546

[52] U.S. Cl. .......... 436/534; 428/402.22; 428/402.24; 525/54.1; 525/54.11; 530/815; 568/583

[58] Field of Search .......... 530/816, 815; 525/54.1, 525/54.11; 428/402, 407; 436/534, 808; 568/583; 435/975, 810

[56] References Cited

U.S. PATENT DOCUMENTS

| | | | |
|---|---|---|---|
| 4,081,246 | 3/1978 | Polito et al. | 530/816 |
| 4,138,383 | 2/1979 | Rembaum et al. | 526/227 |
| 4,181,636 | 1/1980 | Fischer | 424/12 |
| 4,560,504 | 12/1985 | Arnold | 424/85 |
| 4,699,826 | 10/1987 | Schwartz et al. | 525/54.1 |
| 4,877,724 | 10/1989 | Chen et al. | 530/354 |

OTHER PUBLICATIONS

U.S. Ser. No. 238,665; Chen et al.; Aug. 31, 1988.

*Primary Examiner*—Amelia Burgess Yarbrough
*Attorney, Agent, or Firm*—John R. Everett

[57] ABSTRACT

A method for attaching a reactive amine- or sulfhydryl-containing compound to polymeric particles using dication ether salts is disclosed.

26 Claims, No Drawings

ATTACHMENT OF COMPOUNDS TO POLYMERIC PARTICLES USING DICATION ETHERS AND A KIT CONTAINING SAME

FIELD OF THE INVENTION

The present invention relates to the field of immunological testing and diagnosis.

BACKGROUND OF THE INVENTION

Biologically active polypeptides or proteins which are attached to insoluble carrier materials, such as polymeric particles, are used in a variety of ways. For example, the diagnosis of pathological or other conditions in human beings and animals is often carried out using immunological principles for the detection of an immunologically reactive species, for example antibodies or an antigen, in the body fluids of persons or animals. An antigen is a foreign substance, such as a drug, hapten, toxin, lectin, polypeptide or protein which, when introduced into the body, causes the production of antibodies.

Other proteins and amine-containing compounds, such as enzymes, avidin, biotin or polysaccharides, have been covalently linked to various carrier materials for use in affinity chromatography, enzymatic reactions, specific binding reactions and immunoassays.

Carboxylated latex particles are used to prepare diagnostic reagents (U.S. Pat. No. 4,181,636). The conventional procedure for covalently attaching an immunologically reactive species to the particles having surface carboxyl groups involves the use of a water-soluble carbodiimide.

SUMMARY OF THE INVENTION

The present invention provides a method for attaching a reactive amine- or sulfhydryl-containing compound to polymeric particles comprising A. contacting (1) an aqueous suspension of polymeric particles having pendant carboxyl groups on the surface thereof with (2) a dication ether compound to produce reactive intermediate polymer particles having pendant intermediate reactive groups, and B. contacting the reactive intermediate polymer particles produced in step A with a reactive amine- or sulfhydryl-containing compound having a reactive amino or sulfhydryl group, respectively, which reacts with the intermediate reactive groups to form a covalent linkage between the particles and the reactive compound.

This invention also provides a kit comprising: (1) polymeric particles having pendant carboxyl groups on the surface thereof, and (2) a dication ether.

The present invention provides a means for rapidly attaching a reactive amine- or sulfhydryl-containing compound, such as a biologically active polypeptide or protein to insoluble polymeric particles, thereby forming useful materials for immunoassays, diagnostic tests, affinity chromatography, enzymatic reactions and other biological or chemical procedures. The attachment is achieved without adversely affecting the reactive compound which is attached. That is, there is minimal cross-linking or deactivation of the reactive amino or sulfhydryl groups in the reactive compound which participate in the formation of a covalent linkage with pendant carboxyl groups of the particles.

It was initially expected that dication ethers would indiscriminately deactivate the reactive amine or sulfhydryl groups of the reactive compounds. Unexpectedly, we found this not to be the case, and thereby discovered the very useful and efficient attachment method described and claimed herein.

DETAILED DESCRIPTION OF THE INVENTION

The materials prepared according to the method of the present invention can be used in many different chemical and biological procedures. For example, they can be used in affinity chromatography, reactions catalyzed by enzymes, water purification, immunoassays wherein the analyte is an immunologically reactive species which has specific binding affinity for an attached polypeptide or protein, and other processes known to one of ordinary skill in the art. In some instances, the present invention can be used to attach intermediate linking moieties which can be further reacted with compounds of biological interest, such as drugs, hormones, enzymes, antibodies or other proteins or polysaccharides.

One use of the materials prepared by the present invention is as an agglutination immunochemical reagent in an agglutination assay wherein the analyte or material to be detected is an immunologically reactive species found in physiological fluids, cells or tissue extracts of humans or animals, for which an immunological counterpart (or receptor) is available or can be produced. Representative immunologically or biologically reactive species for which the reagent can be used to detect include, but are not limited to, microorganisms (bacteria, protozoa, fungi, viruses and rickettsia), tissue antigens including organ specific antigens, hormones, enzymes, blood cell antigens or other substances found in the blood, plasma proteins, milk proteins, saliva proteins, urine proteins, pathologic proteins, antibodies including autoantibodies and drugs. In such instances, the reactive amine- or sulfhydryl-containing compound used in the method of this invention is an immunological compound which is a receptor for the analyte of interest.

In other embodiments, the material described herein can have an enzyme attached to the particles. Enzymes which can be attached in this manner include those which have reactive amine or sulfhydryl groups which can be reacted according to the present invention with the active pendant groups on the particles without losing enzymatic activity.

In still other embodiments, the material prepared by this invention can be used in competitive binding assays in either a solution or dry format (a dry analytical element), or in what is known in the art as immunometric assays, for example "sandwich" assays.

The method of this invention is a two-step process involving attaching a reactive amine- or sulfhydryl-containing compound which has a reactive amine or sulfhydryl group, respectively, to polymeric particles having outer surface reactive carboxyl groups using a dication ether compound.

Useful dication ethers have the formula:

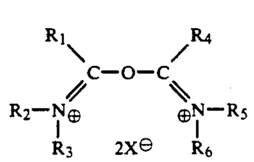

(I)

In this formula, $R_1$ represents hydrogen, alkyl, aralkyl, aryl, alkenyl, $—YR_7$, the group 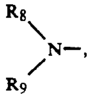

the group 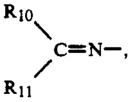

with Y representing sulfur or oxygen, and $R_7$, $R_8$, $R_9$, $R_{10}$, and $R_{11}$ each independently representing alkyl, aralkyl, aryl, or alkenyl.
Alternatively, $R_8$ and $R_9$, or $R_{10}$ and $R_{11}$ may together form a ring structure. $R_{10}$ and $R_{11}$ may each also represent hydrogen. Also, $R_1$ together with $R_2$ may form a heterocyclic ring.

$R_2$ and $R_3$ each independently represents alkyl, aralkyl, aryl, or alkenyl, or, combined with $R_1$ or each other, forms a heterocyclic ring.

$R_4$, $R_5$, and $R_6$ are defined as are $R_1$, $R_2$, and $R_3$, respectively, and are the same as or different from $R_1$, $R_2$, or $R_3$.

$X^{\theta}$ represents an anion or an anionic portion of the compound to form an intramolecular salt.

Dication ethers of formula (I) are described in further detail below.

$R_1$ represents hydrogen, alkyl, aralkyl, aryl, alkenyl, $—YR_7$, the group 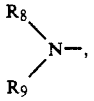

the group 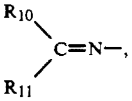

with Y representing sulfur or oxygen, and $R_7$, $R_8$, $R_9$, $R_{10}$, and $R_{11}$ each independently representing alkyl, aralkyl, aryl, or alkenyl. Alternatively, $R_8$ and $R_9$, or $R_{10}$ and $R_{11}$ may together form a ring structure. $R_{10}$ and $R_{11}$ may each also represent hydrogen. Also, $R_1$ together with $R_2$ may form a heterocyclic ring, which may be further condensed with another ring.

Preferably, $R_1$ is hydrogen, alkyl of 1 to 20 carbon atoms (e.g., methyl, ethyl, butyl, 2-ethylhexyl, or dodecyl), aralkyl of from 7 to 20 carbon atoms (e.g., benzyl, phenethyl), aryl of from 6 to 20 carbon atoms (e.g., phenyl, naphthyl), alkenyl of from 2 to 20 carbon atoms (e.g., vinyl, propenyl), the group 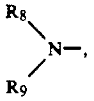

the group 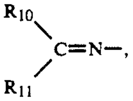

$R_1$ can combine with $R_2$ or $R_3$ to form a heterocyclic ring of 5 to 8 atoms. This ring contains the nitrogen atom to which $R_2$ and $R_3$ are attached in formula (I) and may contain an additional nitrogen atom, or an oxygen or sulfur atom. Examples of such rings include pyridine, quinoline, isoquinoline, thiazole, benzothiazole, thiazoline, oxazole, benzoxazole, imidazole, benzimidazole, and oxazoline.

$R_7$, $R_8$, $R_9$, $R_{10}$, and $R_{11}$ are preferably alkyl of 1 to 20 carbon atoms (e.g., methyl, ethyl, butyl, 2-ethylhexyl, or dodecyl), aralkyl of from 7 to 20 carbon atoms (e.g., benzyl, phenethyl), aryl of from 6 to 20 carbon atoms (e.g., phenyl, naphthyl), or alkenyl of from 2 to 20 carbon atoms (e.g., vinyl, propenyl).

$R_8$ and $R_9$, or $R_{10}$ and $R_{11}$ can also combine to form a ring structure of 5 to 8 atoms. The $R_8$–$R_9$ ring contains the nitrogen atom to which $R_8$ and $R_9$ are attached, and may also contain an additional nitrogen atom, or an oxygen or sulfur atom. The $R_{10}$–$R_{11}$ ring may also contain one or more nitrogen atoms, an oxygen atom, a sulfur atom, or any combination thereof. Examples of such rings include pyrrolidine, piperidine, and morpholine.

$R_2$ and $R_3$ each independently represents alkyl, aryl, aralkyl, alkenyl, or may combine with $R_1$ or each other to form a heterocyclic ring. Preferably, $R_2$ or $R_3$ may each be alkyl of 1 to 20 carbon atoms (e.g., methyl, ethyl, butyl, 2-ethylhexyl, or dodecyl), aralkyl of from 7 to 20 carbon atoms (e.g., benzyl, phenethyl), aryl of from 6 to 20 carbon atoms (e.g., phenyl, naphthyl), or alkenyl of from 2 to 20 carbon atoms (e.g., vinyl, propenyl). $R_2$ and $R_3$ also preferably combine with each other to form a heterocyclic ring of 5 to 8 atoms. This ring contains the nitrogen atom to which $R_2$ and $R_3$ are attached, and may also contain an additional nitrogen atom, or an oxygen or sulfur atom. Examples of such rings include pyrrolidine, piperidine, and morpholine. Either of $R_2$ or $R_3$ can combine with $R_1$ to form a heterocyclic ring, as described above in reference to $R_1$.

$R_4$, $R_5$, and $R_6$ are defined the same as described above for $R_1$, $R_2$, and $R_3$, respectively. $R_4$, $R_5$, and $R_6$ may each be the same as or different from $R_1$, $R_2$, and $R_3$.

$X^{\ominus}$ represents an anion or an anionic portion of the compound, which forms an intramolecular salt. Any anion that forms a salt compound according to formula (I) that is useful to form biological and diagnostic reagents according to the invention can be used. Preferred anions include a sulfonate ion such as methylsulfonate or p-toluenesulfonate $CF_3SO_3^{\ominus}$, $BF_4^{\ominus}$, $PF_6^{\ominus}$, and $ClO_4^{\ominus}$.

In addition to the above-described alkyl, aralkyl, aryl, alkenyl, and heterocyclic groups, groups also useful as $R_1$, $R_2$, $R_3$, $R_4$, $R_5$, $R_6$, $R_7$, and $R_8$ include substituted alkyl, aralkyl, aryl, alkenyl, and heterocyclic groups. Useful substituents include halogen, alkoxy of from 1 to 20 carbon atoms, aryloxy of from 6 to 20 carbon atoms, a sulfo group, N,N-disubstituted carbamoyl, N,N-disubstituted sulfamoyl, and other groups known to those skilled in the art that do not prevent the compounds from functioning as reactive intermediates according to the invention.

Examples of compounds of formula (I) are shown below in Table I.

TABLE I
| | Dication Ether Number |
|---|---|
| 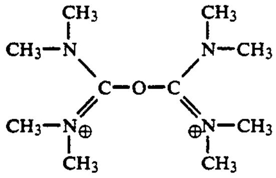 $2CF_3SO_3^{\ominus}$ | 1 |
| 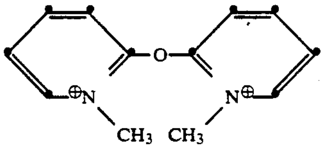 $2CF_3SO_3^{\ominus}$ | 2 |
| 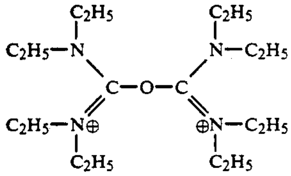 $2CF_3SO_3^{\ominus}$ | 3 |
| 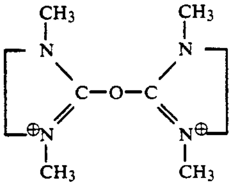 $2CF_3SO_3^{\ominus}$ | 4 |
| 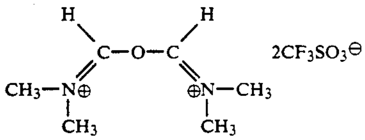 $2CF_3SO_3^{\ominus}$ | 5 |
| 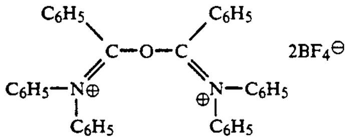 $2BF_4^{\ominus}$ | 6 |
| 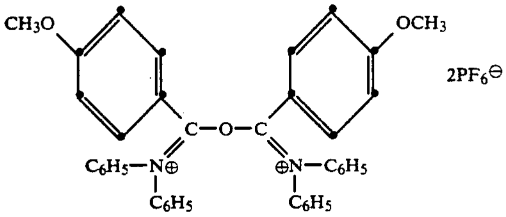 $2PF_6^{\ominus}$ | 7 |
| 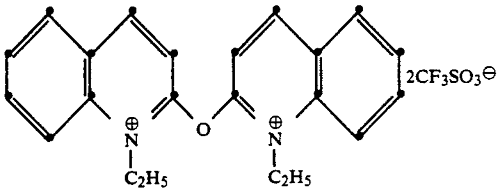 $2CF_3SO_3^{\ominus}$ | 8 |

TABLE I-continued
| | Dication Ether Number |
|---|---|
| 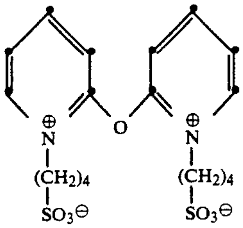 | 9 |
| 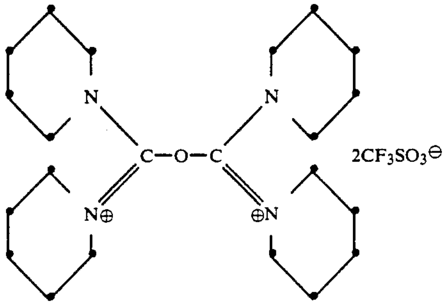 | 10 |
| 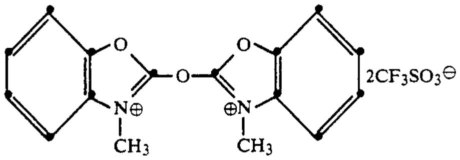 | 11 |
| 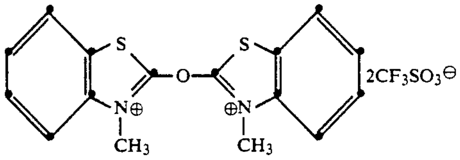 | 12 |
| 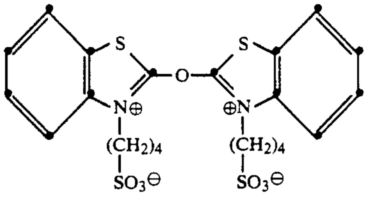 | 13 |
| 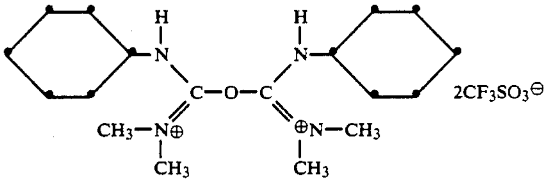 | 14 |
| 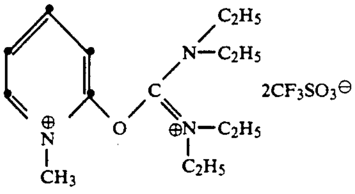 | 15 |

TABLE I-continued
| | Dication Ether Number |
|---|---|
| 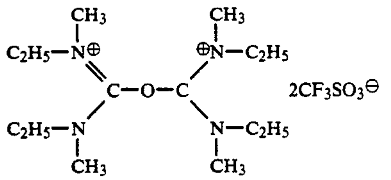 | 16 |
| 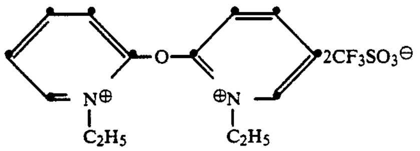 | 17 |
| 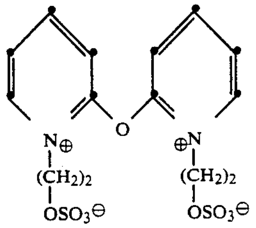 | 18 |
| 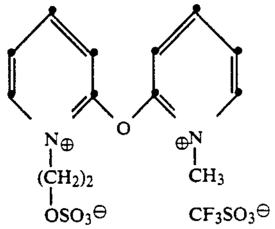 | 19 |
| 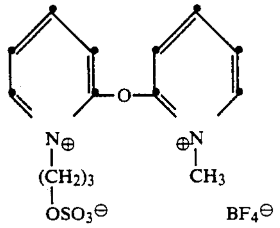 | 20 |
| 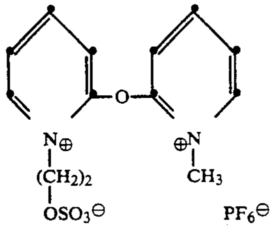 | 21 |
| 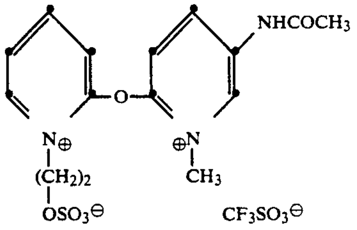 | 22 |

TABLE I-continued
| | Dication Ether Number |
|---|---|
| 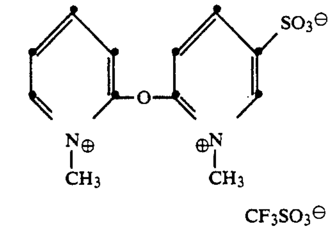 | 23 |
| 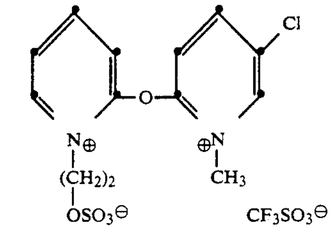 | 24 |
| 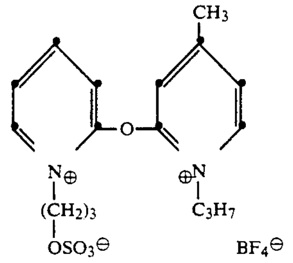 | 25 |
| 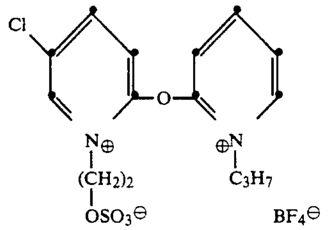 | 26 |
| 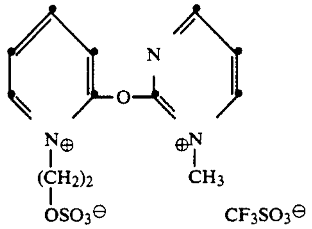 | 27 |
| 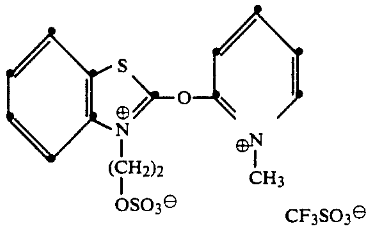 | 28 |

TABLE I-continued
| | Dication Ether Number |
|---|---|
| 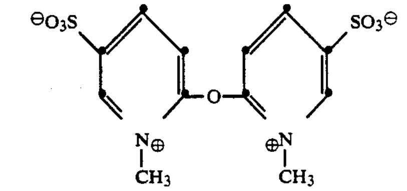 | 29 |
| 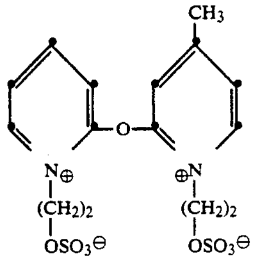 | 30 |
| 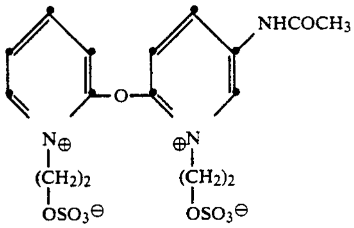 | 31 |
| 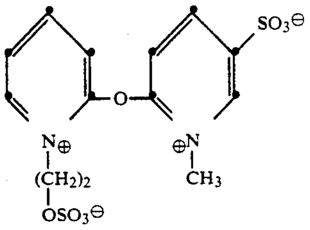 | 32 |
| 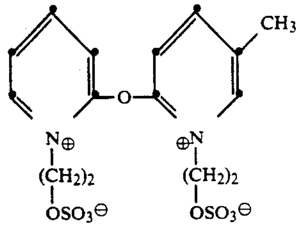 | 33 |
| 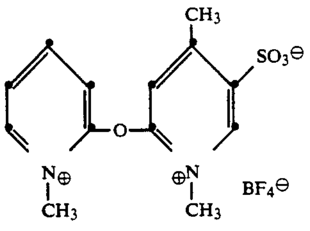 | 34 |
| 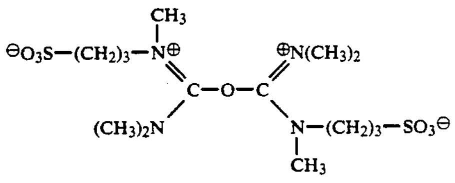 | 35 |

TABLE I-continued

| | Dication Ether Number |
|---|---|
| 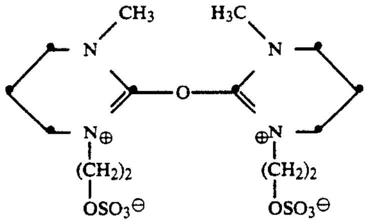 | 36 |
| 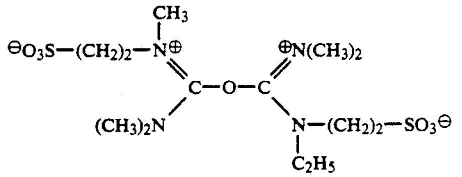 | 37 |

The ethers of formula (I) can be made by techniques known to those skilled in the chemical synthesis art. Useful synthesis techniques include those described in Journal of the American Chemical Society, 103, 4839 (1981). The preparation of compounds of formula (I) is further described below in the synthesis examples.

SYNTHESIS EXAMPLE 1

Bis(tetramethylformamidinium) ether ditriflate (Ether 1, Table 1)

To a solution of 11.6 g tetramethylurea in 100 ml $CH_2Cl_2$, 16.8 ml of triflic anhydride in 50 ml $CH_2Cl_2$ was added dropwise. The mixture was evaporated on a rotatory evaporator at room temperature to yield a yellowish oily residue. The residue was dissolved in 100 ml $CH_2Cl_2$ and 11.6 g tetramethylurea in 50 ml $CH_2Cl_2$ was added, at which point a precipitate was formed. The mixture was stirred under nitrogen overnight, after which the precipitate was filtered, washed with $CH_2Cl_2$, and dried to obtain a colorless crystalline material with a melting point of 258°-260° C. IR and NMR analysis indicated that the crystalline material was bis(-tetramethylformamidinium) ether ditriflate.

SYNTHESIS EXAMPLE 2

Bis(1-methyl-2-pyridinium) ether ditriflate (Ether 2, Table 1)

To a solution of 0.2 moles of N-methyl-2-pyridone in 150 ml $CH_2Cl_2$, 16.8 ml of triflic anhydride was added dropwise. A precipitate formed and the mixture was stirred under nitrogen at room temperature for 72 hours. The precipitate was filtered, washed with $CH_2Cl_2$, and dried to yield a colorless crystalline material with a melting point of 193°-195° C. IR and NMR analysis indicated that the material was bis(1-methyl-2-pyridinium) ether ditriflate.

SYNTHESIS OF POLYMERIC PARTICLES

The polymeric particles useful in the method of this invention are generally water-insoluble particles having a particle size in the range of from about 0.01 to about 100 micrometers, and preferably from about 0.1 to about 3 micrometers. They can be homogeneous polymeric particles meaning that they are composed of the same polymer throughout, or they can be particles composed of more than one polymer such as graft copolymers as described, for example, in U.S. Pat. No. 3,700,609 (issued Oct. 24, 1972 to Tregear et al) and core-shell polymers described for example in U.S. Pat. No. 4,401,765 (issued Aug. 30, 1983 to Craig et al). It is critical that the polymeric particles have surface carboxyl groups available for attachment of the reactive amine- or sulfhydryl-containing compound. Such groups are preferably added to the particles by incorporating monomers containing such groups into the polymers (for example, acrylic acid, methacrylic acid, itaconic acid, and the like). Alternatively, they can be added to the particles by further chemical reaction of a polymer having other precursor reactive groups which can be converted to carboxyl groups (for example, by hydrolysis of anhydrides, such as maleic anhydride, or by oxidation of surface methylol or aldehyde end groups).

Generally, useful polymeric particles can be prepared using any suitable polymerization technique, including emulsion (including batch, semi-continuous and continuous) and suspension polymerization techniques, graft copolymerization, and others known to one skilled in the polymer chemistry art. Continuous emulsion polymerization is preferred as it can be used to provide generally smaller particles without the use of surfactants or emulsifiers as described for example in U.S. Pat. No. 4,415,700 and Research Disclosure publication 15963 (July, 1977). Research Disclosure is a publication available from Kenneth Mason Publications, Ltd., The Old Harbourmaster's, 8 North Street, Emsworth, Hampshire P010 7DD, England. Continuous emulsion polymerization is the most preferred technique, as described in the noted *Research Disclosure* publication.

Useful carboxylated particles are prepared from carboxylated styrene and its derivatives, carboxylated styrene-butadiene copolymers, acrylic and methacrylic acid polymers and other materials, many of which are commercially available.

Preferably, the polymeric particles are composed of a polymer represented by the structure:

$$-(A)_x-(B)_{100-x}-$$

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers.

Monomers from which A can be derived include, but are not limited to, acrylic and methacrylic acids, itaconic acid, aconitic acid, fumaric acid, maleic acid, β-carboxyethyl acrylate, β-carboxyethyl methacrylate, m&p-carboxymethylstyrene, methacrylamidohexanoic acid and N-(2-carboxy-1,1-dimethylethyl)acrylamide or a salt or anhydride precursor thereof. Acrylic and methacrylic acids, itaconic acid, aconitic acid, fumaric acid, maleic acid, β-carboxyethyl acrylate, β-carboxyethyl methacrylate or a salt or anhydride precursor thereof are preferred in the practice of this invention. Monomers from which B can be derived include, but are not limited to, styrene and styrene derivatives (for example vinyltoluene, 4-t-butylstyrene, divinylbenzene and 2-chloromethylstyrene), acrylic and methacrylic acid esters (for example, methyl acrylate, ethyl methacrylate, n-butyl 1 acrylate, 2-ethylhexyl methacrylate, methyl methacrylate, 2-hydroxyethyl methacrylate, methacrylamide, ethylene dimethacrylate and 2-hydroxyethyl acrylate), sodium 2-acrylamido-2-methylpropane-sulfonate, sodium 3-acryloyloxypropanesulfonate, p-styrenesulfonate, or acrylonitrile. Preferably, B is derived from styrene or a styrene derivative, or an acrylic or methacrylic acid ester.

For both the A and B monomers, it is important that the specific monomers used and their proportions be chosen so as to render the particles water-insoluble.

In the structure identified above, x is from about 0.1 to about 70, and preferably from about 1 to about 20, mole percent.

Representative polymers of which the polymeric particles are composed include poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m&p-divinylbenzene) (89:10:1 molar ratio), poly(styrene-co-2-carboxyethyl acrylate) (90:10 molar ratio), poly(methyl methacrylate-co-acrylic acid) (70:30 molar ratio) and poly(styrene-co-butyl acrylate-co-methacrylic acid)(45:45:10 weight ratio).

In one embodiment, the particles are core-shell particles wherein the core is composed of a first polymer, and the shell is composed of a second polymer. The second polymer must have reactive carboxyl groups or groups which can be converted to carboxyl groups prior to attachment of the polypeptide or protein The polymeric particles described herein can be supplied as a dried powder which can be resuspended for any use or interest. Preferably, however, they are supplied as an aqueous suspension generally having from about 0.1 to about 35 percent solids. Suspending agents, buffers or other addenda can be included in the suspension if desired.

The mechanism by which the dication ethers activate carboxyl containing polymers for reaction with amine or sulfhydryl groups is as follows:

STEP 1

-continued

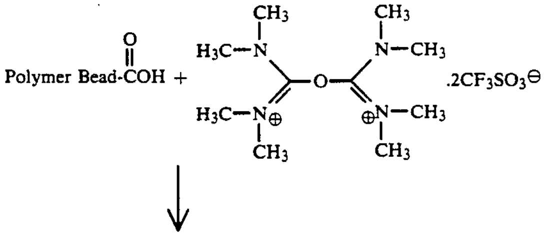

Intermediate 1

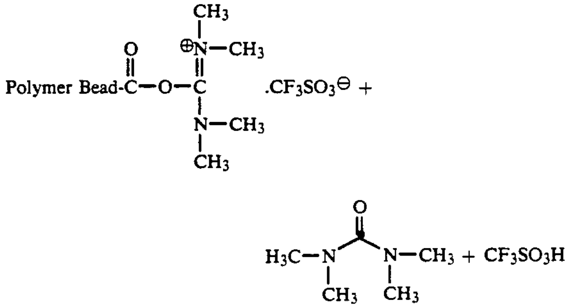

STEP 2

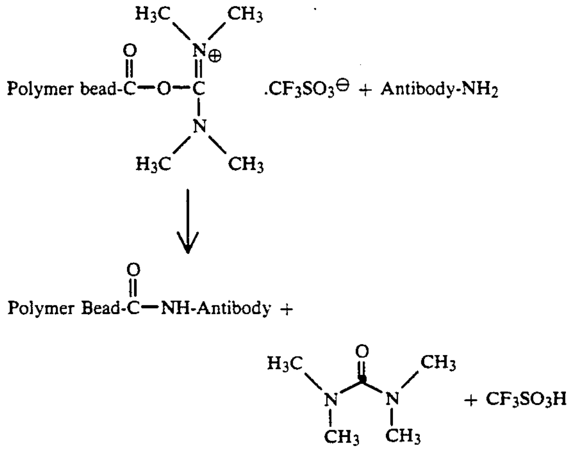

Based on this mechanism it is believed that the dication ethers defined by formula 1, supra, would all activate carboxyl polymers in the same manner. All diction ethers in this class would activate carboxyl polymers via identical mechanisms due to their unique structure; bis(carbenium ions) linked by a heteroatom-containing lone pair electrons.

Any reactive amine- or sulfhydryl-containing compound can be attached to polymeric particles according to the present invention as long as that compound contains a reactive amine or sulfhydryl group, respectively, which will react with the intermediate formed by the reaction of the dication ether compound with carboxyl groups on the particles. Such compounds include, but are not limited to, monoamines, monohydrazides, diamines, dihydrazides, enzymes, biotin or derivatives thereof, avidin or derivatives thereof, amino acids, peptides, polypeptides, proteins, mono- oligo- and poly-saccharides, and others which would be apparent to one skilled in the art. In certain embodiments, the reactive amine- or sulfhydryl-containing compound is a polypeptide or protein which is biologically active. The term "biologically active" refers to its capacity for interaction with another component which may be found in physiological fluids. Such an interaction can be catalytic activity in the case where the material is an enzyme. In addition, the interaction can be a complexation which occurs between materials which have affinity for one another, such as avidin with biotin or antibodies with antigens, and the like. In other embodiments, the reactive amine- or sulfhydryl-containing compound is a diamine, polysaccharide, amino acid, peptide or protein which can be a linking moiety for attaching a second compound to the particle. Such second compounds include, but are not limited to, enzymes, antibodies, antigens, drugs, biotin or derivatives thereof and others readily apparent to one skilled in the art.

Preferably, the reactive amine- or sulfhydryl-containing compound is an immunologically reactive species, including but not limited to the biological and chemical compounds listed above. More preferably, it is an antibody, such as an antibody directed against a drug, hormone, Streptococcus A antigen, a chlamydial antigen, a gonococcal antigen, human chorionic gonadotropin, human leutinizing hormone or a herpes virus. Alternatively, the immunologically reactive species can be an antigen, such as an antigen of HTLV-I or HIV-I.

In certain embodiments, the materials prepared by the method of this invention can have a tracer associated therewith. A tracer is a detectable species which enables one to detect the reagent. Useful tracers include radioisotopes, colorimetric or fluorometric compounds, enzymes, chemiluminescent compounds, phosphorescent compounds and others known to one skilled in the art. Particularly useful tracers are colorimetric and fluorometric compounds. The tracer can be associated with the reagent in any suitable manner. For example, the tracer can be associated (for example, covalently or ionically attached) with the reactive amine- or sulfhydryl-containing-compound. Alternatively and preferably, the tracer is associated with the polymeric particles, for example attached (covalently or adsorbed) to their outer surface or internally distributed in part or all of the volume, or both.

It is particularly desirable to incorporate tracers such as colorimetric or fluorometric dyes into the particles. Such incorporation can be accomplished by polymerizing monomers having dye or dye precursor moieties attached to the polymerizable vinyl group. Preferably, however, the dyes are "loaded" into the particles after their formation using procedures such as described in pending U.S. Ser. No. 347,537, filed May 4, 1989.

Particularly useful tracers which can be incorporated into particles include cyan, yellow and magenta dyes, europium and other rare earth chelates (such as a mixture of europium-thenoyl trifluoroacetonate and trioctylphosphine oxide), fluoroescent dyes such as 2,5-bis(6-butyl-2-benzoxazolyl)thiophene and 3-(2-benzothiazolyl)-7-diethylaminocoumarin and others known in the art. Incorporation of dyes can be achieved using the techniques described in U.S. Pat. No. 4,199,363 (issued Apr. 22, 1980 to Chen) and in copending and commonly assigned U.S. Ser. No. 344,870, filed Apr. 28, 1989, by Sutton, both incorporated herein by reference.

The method of the present invention is carried out in two steps, the first of which involves contacting an aqueous suspension of the polymeric particles described above with a dication ether to produce reactive intermediate polymer particles having intermediate reactive groups in place of the carboxyl groups. This step is carried out at a suitable pH using suitable acids or buffers to provide the desired pH. Generally, the pH is 6.0 or less, but this is not critical as long as the reaction can proceed. More likely, the pH is between about 3.5 and about 6. The molar ratio of dication ether to the carboxyl groups on the surface of the particles is from about 10:1 to about 1000:1, and preferably from about 50:1 to about 400:1.

In the second step of the method, the reactive intermediate formed in the first step is contacted with a reactive amine- or sulfhydryl-containing compound having a reactive amine or sulfhydryl group, respectively, which will react with the intermediate reactive group of the reactive intermediate. A covalent linkage is thereby formed between the particles and the reactive compound.

This second step can be carried out at a suitable pH such that the desired reaction occurs without premature agglutination. The pH may be varied depending upon the reactants involved and their concentration in the reaction medium. For many amino- or sulfhydryl-containing compounds, this pH will be greater than 6. The weight ratio of the protein to polymer particles can range from about 1:200 to about 1:10 and is preferably about 1:75 to about 1:20.

The method of the invention is generally carried out at a temperature of from about 10° to about 60° C., and preferably from about 15 to about 30° C. The temperature can be the same or different for the two steps of the method.

Further details regarding the method of this invention would be readily apparent to one of ordinary skill in the art from the representative examples described below.

The polymeric particles described above can be provided in a kit which also includes one or more dication ethers as described herein. The particles can be free of tracer, or have a tracer associated therewith. Useful tracers are noted above, but preferred tracers include colorimetric and fluorometric dyes which have been incorporated into the particles in a suitable manner. The particles can be supplied as a powder as long as it can be resuspended for any use of interest. Preferably, they are supplied as an aqueous suspension as described above.

Such kits can optionally include a compound having reactive amine or sulfhydryl groups for attachment to the polymeric particles in the method of this invention. Other optional materials include pipettes, test tubes, instructions, buffers or other reagents and equipment which may be helpful in the practice of the invention.

The following examples illustrate the practice of this invention.

EXAMPLE 1

Activation of Carboxyl Group-Containing Beads with a Dication Ether Salt and Covalent Reaction with Bovine Gamma Globulin Antibody Dication ether salt (Number 1, Table 1) (66 mg, 0.13 mmol) was added to 100 mg (dry weight) of poly(styrene-co-methacrylic acid) (mole ratio 90/10) polymer beads in 30 mL of 0.1M pH 6.0 phosphate buffer or 0.1M pH 6.0 2-(4-morpholino)-ethanesulfonic acid (MES) buffer in a 50 mL polypropylene centrifuge tube. The centrifuge tube was rotated end-over-end for 10 minutes at 30–35 rpm while attached to a rotating plate mounted at a 45° angle. Then 1 mg of tritiated radioactive bovine gamma globulin ($^3H$ BGG) was added to the reaction mixture. Rotation was continued for an additional 24 hours. The reaction was quenched by addition of excess bovine serum albumin (BSA) (100 mg, 50 mg/mL in the phosphate buffer stated above). The sample was incubated an additional 24 hours.

In one variation of the above experiment, the reaction was centrifuged (10,000 rpm, 30 minutes) 10 minutes after the addition of the dication ether salt. After centrifugation, the supernatant was discarded and the beads resuspended in 30 mL of the appropriate buffer. This was followed by addition of the 1 mg $^3H$ BGG and quenching as described.

A control reaction was prepared by incubating the same amount of beads as above with 1 mg $^3H$ BGG except that the beads were not first activated with the dication ether salt. The control was rotated end-over-end, then quenched with BSA as described hereinbefore.

The total amount of antibody ($^3H$ BGG) bound was determined by measuring: a) the total cpm (counts per minute) in a 500 μL aliquot of the reaction, b) the cpm remaining in the supernatant following centrifugation of a 1 mL sample of the reaction, and c) the cpm bound to the latex following repeated washes of the pellet obtained in b). The fraction of the $^3H$ BGG which is covalently bound to the beads was determined following incubation of the reacted beads in the presence of 1% sodium dodecysulfate (SDS) at 37° C. for about 24 hours with end-over-end rotation. The same procedure described above for determining the total amount of antibody bound was used to determine the amount of antibody covalently bound. The results are shown in Tables II and III.

TABLE II (Before SDS Treatment)

| Sample | Activating Agent | Buffer | Centrifuged | % Bound | mg BGG g Polymer |
|---|---|---|---|---|---|
| 1 | Dication ether 1 Table 1 | MES | Yes | 89.2 | 8.9 |
| 2 | Dication ether 1 Table 1 | MES | No | 86.8 | 8.7 |
| 3 | Dication ether 1 Table 1 | phosphate | Yes | 86.1 | 8.6 |
| 4 | Dication ether 1 Table 1 | phosphate | No | 90.6 | 9.1 |
| 5 | None (Control) | phosphate | No | 58.6 | 5.9 |

TABLE III (After SDS Treatment)

| Sample | Activating Agent | Buffer | Centrifuged | Covalently Bound % |
|---|---|---|---|---|
| 1 | Dication ether 1 Table 1 | MES | Yes | 70.4 |
| 2 | Dication ether 1 Table 1 | MES | No | 87.5 |
| 3 | Dication ether 1 Table 1 | phosphate | Yes | 65.4 |
| 4 | Dication ether 1 Table 1 | phosphate | No | 67.8 |
| 5 | None (Control) | phosphate | No | 1.4 |

This example demonstrates that $^3H$-BGG can be covalently bound to carboxylate beads using a dictation ether salt as an activating agent. Because the reactive intermediate between the bead and the dictation ether salt is stable to centrifugation one can add the $^3H$-BGG after centrifugation and still retain high levels of covalently bound antibody.

The following Example 2 shows that the method of this invention preserves the activity of the antibody in an enzyme label binding experiment.

EXAMPLE 2

A monoclonal anti-phenobarbital antibody was reacted with carboxyl beads which had been activated with the dication ether salt 1, Table 1 employed in Example 1.

The antibody employed was an in-house prepared monoclonal antibody specific for phenobarbital (Phe 1.9). This antibody was prepared at Eastman Kodak Company by immunization of Balb c mice with a conjugate of phenobarbital-human serum albumin. Spleens of the immunized mice were fused with myeloma (SP2/0-Ag 14) cells to generate the hybridomas. This preparatory method used known procedures. The mass of the antibody bound to the beads was determined in a parallel experiment in which $^3H$ BGG was substituted for the anti-phenobarbital antibody. The amount of active antibody bound to each bead was compared in the enzyme label binding experiment described below.

A sample of the polymer beads employed in Example 1 (30 mg dry weight) was activated with the dictation ether salt employed in Example 1 (23 mg, 0.045 mmol) in 10 mL of 0.1M pH 6.0 MES buffer. This preparation was mixed with 1.5 mg of the Phe 1.9 antibody.

A second sample of the beads was activated with the dication ether salt 2 from Table I (22.5 mg, 0.045 mmol) in 10 mL of 0.1M pH 6.0 MES buffer and mixed with 1.5 mg of Phe 1.9 antibody.

One additional bead sample 3 was activated exactly as samples 1 and 2, except after addition of the activating agents, the sample 3 was centrifuged (10,000 rpm for 30 minutes). After centrifugation, the supernatant was discarded and the beads resuspended in 10 mL of the same buffer. This was followed by addition of 1.5 mg Phe 1.9 antibody to separate identical samples 1 and 2.

All samples were incubated with end-over-end rotation at room temperature for 24 hours. Reactions in the samples were stopped by the addition of BSA (30 mg, 30 mg/mL). The incubation was continued for about 4 more hours. The samples were centrifuged. The supernatants were discarded. The pellets were washed twice with PBS (phosphate buffered saline, pH=7.4) and resuspended in PBS.

The mass of antibody bound to the beads in each sample was determined by assaying the number of counts for samples ran in parallel to samples 1-3, supra, having $^3H$ BGG bound to the carboxyl bead by exactly the same procedures and in the same amounts as in samples 1-3. The covalent/total ratio was calculated as described in Example 1 after SDS incubation.

The relative amount of active antibody in each preparation was determined in an assay in which serial dilutions of the beads ($6.3\times10^{-10}$M to $2.0\times10^{-7}$M theoretical phenobarbital binding sites based on the mass of antibody bound) were mixed with a fixed concentration of a phenobarbital-glucose oxidase enzyme label ($5\times10^{-10}$M). The bead dilutions and label were incubated for about 2 hours with constant agitation at room temperature in phosphate buffered saline containing 1% bovine serum albumin. The amount of phenobarbital-glucose oxidase label remaining in solution following centrifugation was determined and the concentration of phenobarbital binding sites required to bind 50% of the enzyme label was determined. The results are summarized in Tables IV and V.

TABLE IV

| MASS BINDING EXPERIMENT | | | | | |
|---|---|---|---|---|---|
| Sample | Activating Agent | Centrifuged | % Bound | mg BGG g polymer | Ratio Covalent Total |
| 1 | Dication ether 1 | No | 77.3 | 38.6 | 0.94/1 |
| 2 | Dication ether 2 | No | 79.7 | 39.9 | 0.99/1 |
| 3 | Dication Ether 1 | Yes | 70.0 | 35.0 | 0.57/1 |

TABLE V

| LATEX ENZYME LABEL TITRATION | | | |
|---|---|---|---|
| Sample | Activating Agent | Centrifuged | nmolar Theoretical Phenobarbital Binding Sites Where 50% of the Enzyme Label is Bound |
| 1 | Dication ether 1 | No | 13 |
| 2 | Dication ether 2 | No | 14 |
| 3 | Dication Ether 1 | Yes | 10 |

This example demonstrates that antibody can be covalently bound to carboxylated beads using a dictation ether salt as an activating agent. In addition, it demonstrates that the antibody can be attached to dication ether activated carboxylated beads while preserving antibody activity. When reaction mixtures are centrifuged, the dication ether salts offer an advantage in that the amount of protein covalently bound is high.

The invention has been described in detail with particular reference to preferred embodiments thereof, but it will be understood that variations and modifications can be effected within the spirit and scope of the invention.

We claim:

1. A method for attaching a reactive amine- or sulfhydryl-containing compound to polymeric particles comprising:

A. contacting (1) an aqueous suspension of polymeric particles having pendant carboxyl groups on the surface thereof with (2) a dication ether compound to produce reactive intermediate polymer particles having pendant intermediate reactive groups, and B. contacting the reactive intermediate polymer particles produced in step A with a reactive amine- or sulfhydryl-containing compound having a reactive amine or sulfhydryl group, respectively, which reacts with said intermediate reactive groups to form a covalent linkage between said particles and said reactive compound.

2. The method of claim 1 wherein said reactive amine- or sulfhydryl-containing compound is a polypeptide or protein.

3. The method of claim 1 wherein said dication ether is present in a molar ratio to said carboxyl groups of from about 10:1 to about 1000:1.

4. The method of claim 1 carried out at a temperature of from about 10° C. to about 60° C.

5. The method of claim 1 wherein said dication ether has the structure:

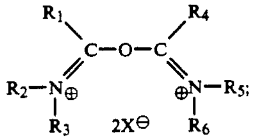

wherein $R_1$ and $R_4$, each independently, represents hydrogen, alkyl, aralkyl, aryl, alkenyl, $—YR_7$, the group

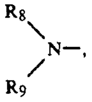

the group

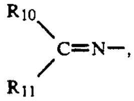

with Y representing sulfur or oxygen, and $R_7$, $R_8$, $R_9$, $R_{10}$, and $R_{11}$ each independently representing alkyl, aralkyl, aryl, or alkenyl. Alternatively, $R_8$ and $R_9$, or $R_{10}$ and $R_{11}$ may together form a ring structure. $R_{10}$ and $R_{11}$ may each also represent hydrogen;

$R_1$ together with $R_2$ may form a heterocyclic ring; and $R_2$, $R_3$, $R_5$ and $R_6$ each independently represents alkyl, aralkyl, aryl, or alkenyl, or, $R_2$ or $R_3$ combined with $R_1$ or each other, or $R_5$ or $R_6$ combined with $R_4$ or each other, form a heterocyclic ring.

$X^{\ominus}$ represents an anion or an anionic portion of the compound to form an intramolecular salt.

6. The method of claim 5 wherein said dication ether is selected from Table 1 as follows:

TABLE I

| | Dication Ether Number |
|---|---|
| 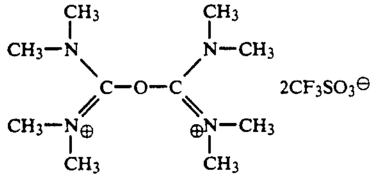 | 1 |
| 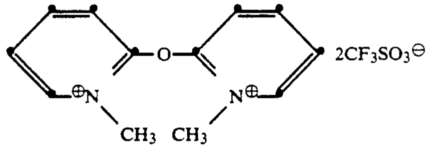 | 2 |

TABLE I-continued
| | Dication Ether Number |
|---|---|
| 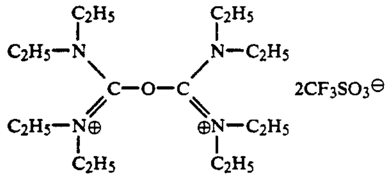 | 3 |
| 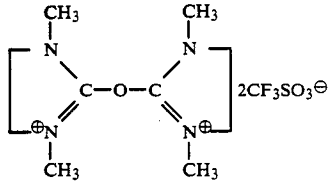 | 4 |
| 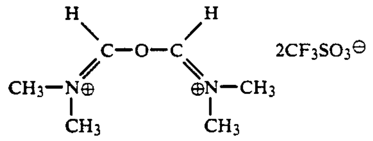 | 5 |
| 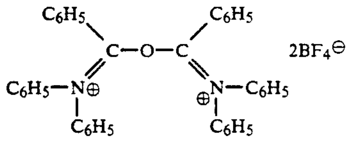 | 6 |
| 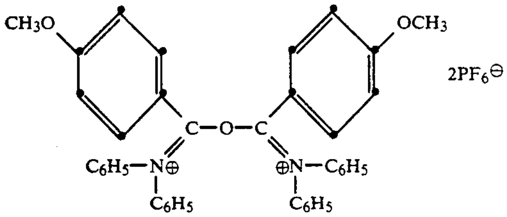 | 7 |
| 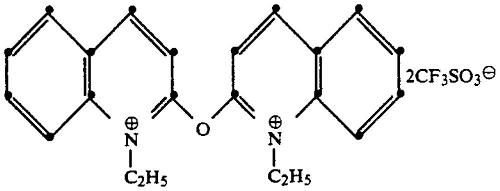 | 8 |
| 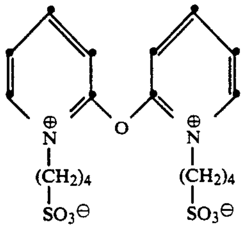 | 9 |

TABLE I-continued
| | Dication Ether Number |
|---|---|
| 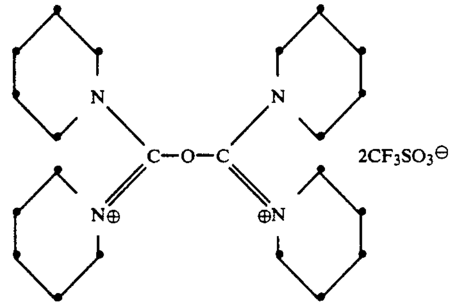 | 10 |
| 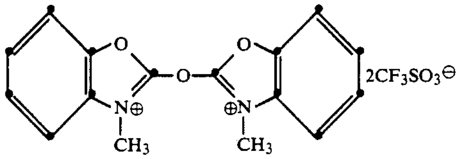 | 11 |
| 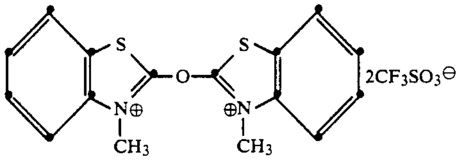 | 12 |
| 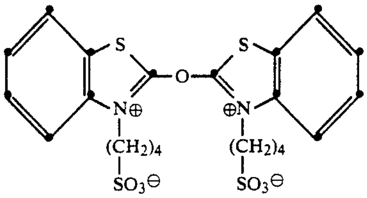 | 13 |
| 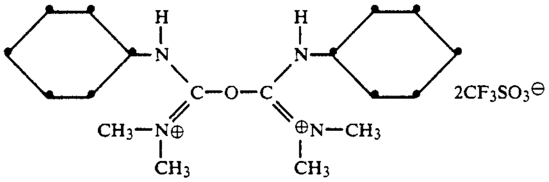 | 14 |
| 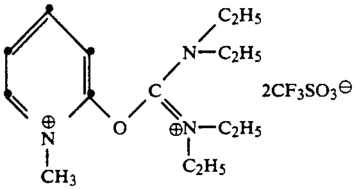 | 15 |
| 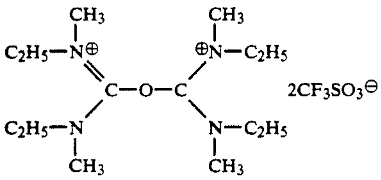 | 16 |
| 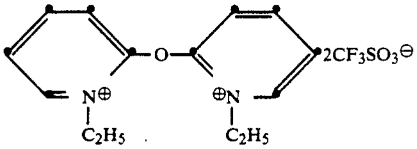 | 17 |

TABLE I-continued
| | Dication Ether Number |
|---|---|
| 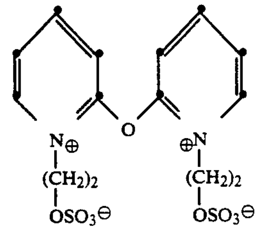 | 18 |
| 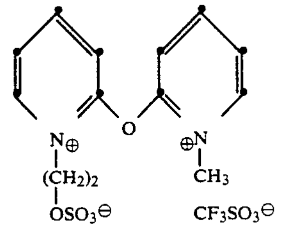 | 19 |
| 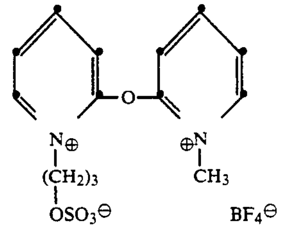 | 20 |
| 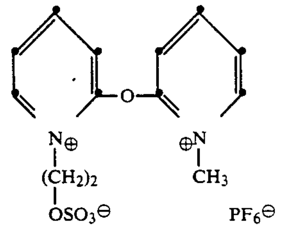 | 21 |
| 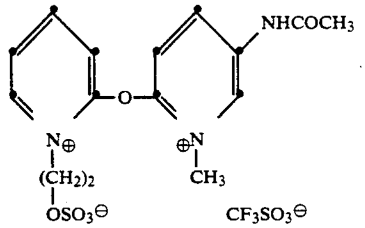 | 22 |
| 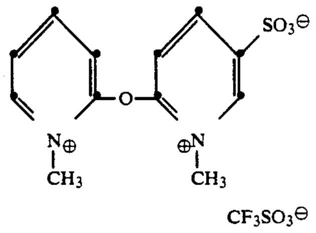 | 23 |

TABLE I-continued
| | Dication Ether Number |
|---|---|
| 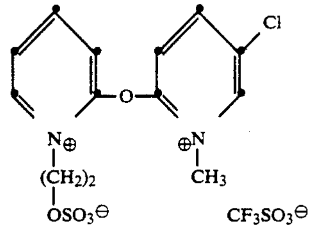 | 24 |
| 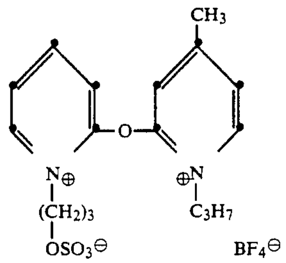 | 25 |
| 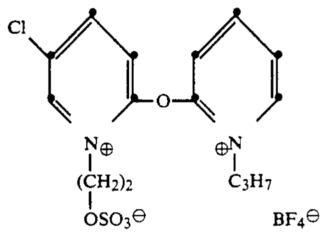 | 26 |
| 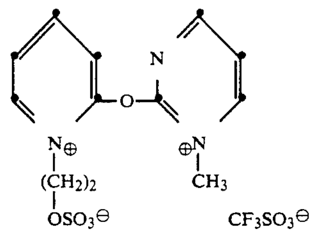 | 27 |
| 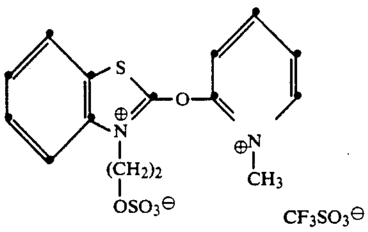 | 28 |
| 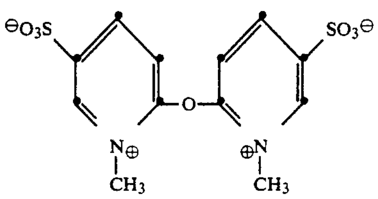 | 29 |

TABLE I-continued
| | Dication Ether Number |
|---|---|
| 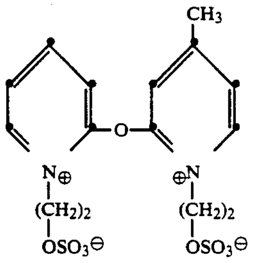 | 30 |
| 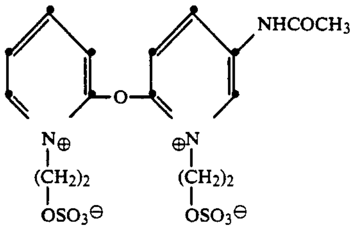 | 31 |
| 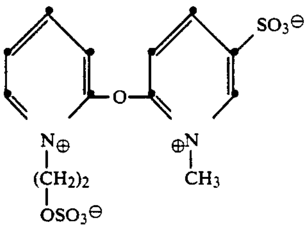 | 32 |
| 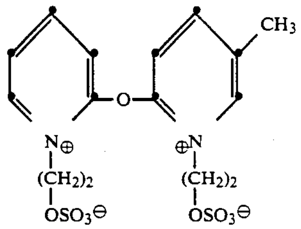 | 33 |
| 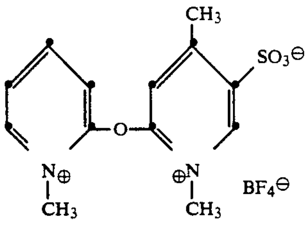 | 34 |
| 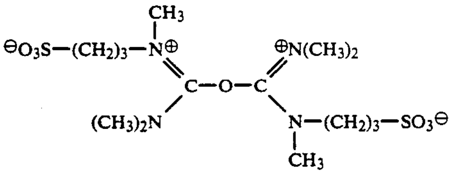 | 35 |
| 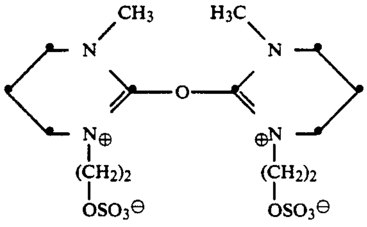 | 36 |

TABLE I-continued

| | Dication Ether Number |
|---|---|
| 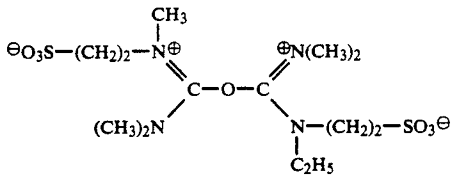 | 37 |

7. The method of claim 6 wherein the dication ether is selected from ethers 1 and 2 of Table 1 as follows:

TABLE I

| | Dication Ether Number |
|---|---|
| 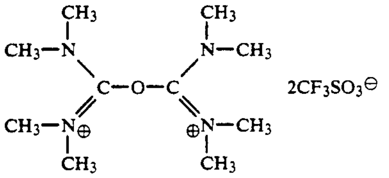 | 1 |
| 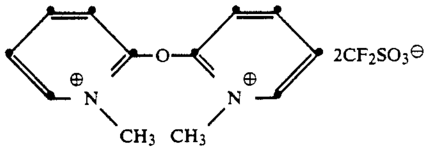 | 2. |

8. The method of claim 2 wherein said polymeric particles are composed of a polymer represented by the structure:

$$-(A)_x-(B)_{100-x}$$

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers, and x is from about 0.1 to about 70 mole percent.

9. The method of claim 8 wherein said polymeric particles are composed of the defined polymer wherein A is derived from acrylic acid, methacrylic acid, itaconic acid, β-carboxyethyl acrylate, β-carboxyethyl methacrylate, m&p-carboxymethylstyrene, methacrylamidohexanoic acid or N-(2-carboxy-1,1-dimethylethyl)acrylamide, or a salt or anhydride precursor thereof, and B is derived from styrene or a styrene derivative, an acrylic or methacrylic acid ester, or acrylonitrile and x is from about 1 to about 20 mole percent.

10. The method of claim 7 wherein said polymeric particles are composed of poly(styrene-co-vinylbenzyl chloride-co-acrylic acid), poly(styrene-co-acrylic acid), poly(styrene-co-methacrylic acid), poly(styrene-co-acrylic acid-co-m&p-divinylbenzene) or poly(styrene-co-2-carboxyethyl acrylate).

11. The method of claim 2 wherein the protein is an antibody directed against Streptococcus A antigen, a chlamydial antigen, a gonococcal antigen, human chorionic gonadotropin, human leutinizing hormone or a herpes virus.

12. The method of claim 2 wherein the protein is an antibody against a drug or hormone.

13. A kit comprising: (1) polymeric particles having pendant carboxyl groups on the surface thereof, and (2) a dication ether.

14. The kit of claim 13 further comprising a reactive compound having a reactive amine or sulfhydryl group for attachment to said particles.

15. The kit of claim 14 wherein the compound is an immunologically reactive species.

16. The kit of claim 15 wherein said dication ether has the structure:.b

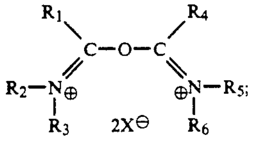

wherein $R_1$ and $R_4$, each independently, represent hydrogen, alkyl, aralkyl, aryl, alkenyl, $-YR_7$, the group 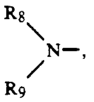

the group 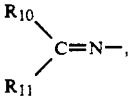

with Y representing sulfur or oxygen, and $R_7$, $R_8$, $R_9$, $R_{10}$, and $R_{11}$ each independently representing alkyl, aralkyl, aryl, or alkenyl. Alternatively, $R_8$ and $R_9$, or $R_{10}$ and $R_{11}$ may together form a ring structure. $R_{10}$ and $R_{11}$ may each also represent hydrogen;

$R_1$ together with $R_2$ may form a heterocyclic ring; and $R_2$, $R_3$, $R_5$ and $R_6$ each independently represent alkyl, aralkyl, aryl, or alkenyl, or, $R_2$ or $R_3$ combined with $R_1$ or each other, or $R_5$ or $R_6$ combined with $R_4$ or each other, form a heterocyclic ring.

$X^{\ominus}$ represents an anion or an anionic portion of the compound to form an intramolecular salt.

17. The kit of claim 16 wherein said polymeric particles are composed of a polymer represented by the structure:

$$-(A)_x-(B)_{100-x}$$

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers, and x is from about 0.1 to about 70 mole percent.

18. The kit of claim 17 wherein said polymeric particles are provided in an aqueous suspension.

19. The kit of claim 17 wherein the dication ether is selected from Table 1 as follows:

TABLE I

| | Dication Ether Number |
|---|---|
| 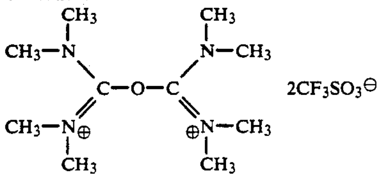 | 1 |
| 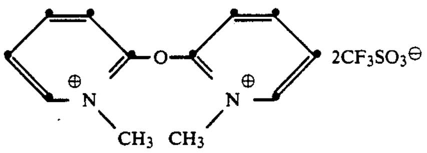 | 2 |
| 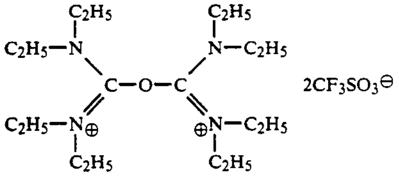 | 3 |
| 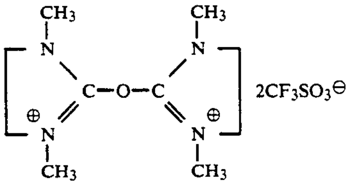 | 4 |
| 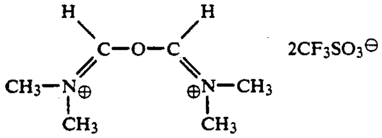 | 5 |
| 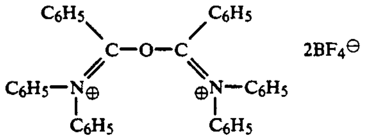 | 6 |
| 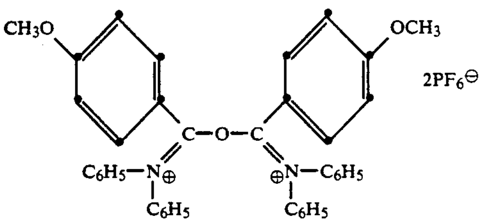 | 7 |

TABLE I-continued

| | Dication Ether Number |
|---|---|
| 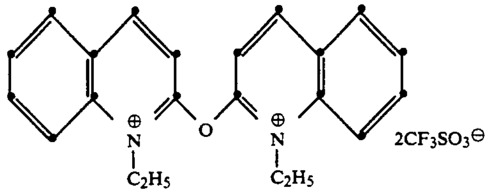 | 8 |
| 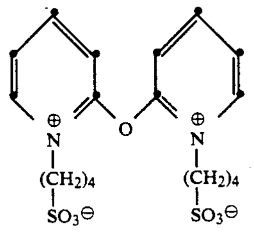 | 9 |
| 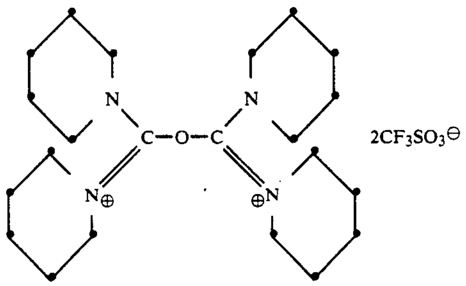 | 10 |
| 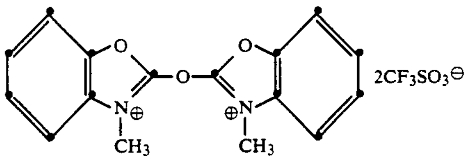 | 11 |
| 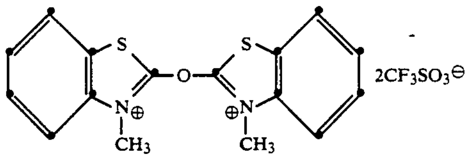 | 12 |
| 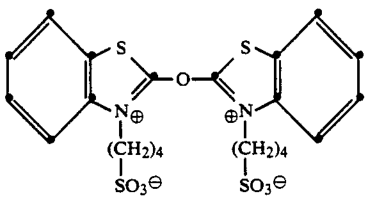 | 13 |
| 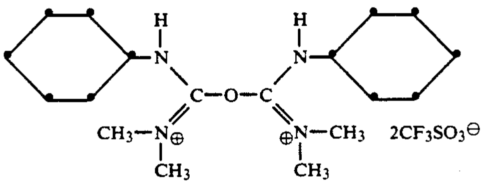 | 14 |

TABLE I-continued
| | Dication Ether Number |
|---|---|
| 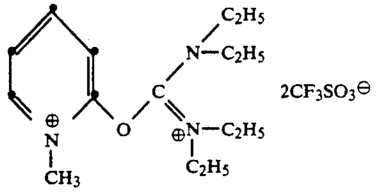 | 15 |
| 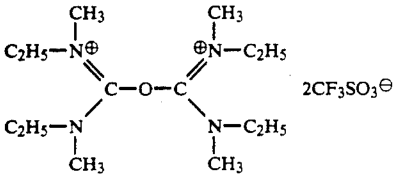 | 16 |
| 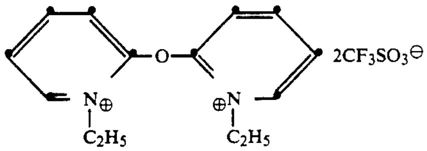 | 17 |
| 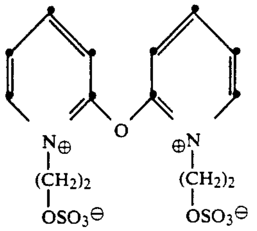 | 18 |
| 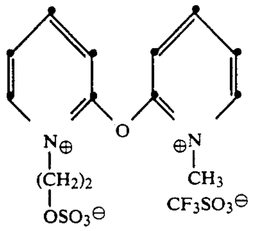 | 19 |
| 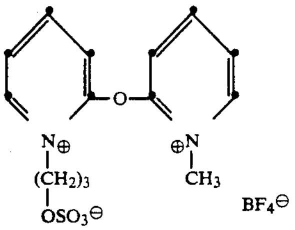 | 20 |
| 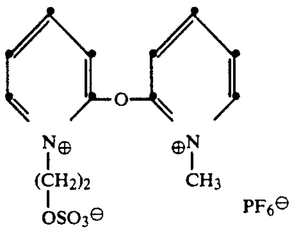 | 21 |
TABLE I-continued
| | Dication Ether Number |
|---|---|
| 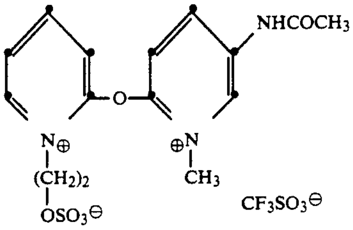 | 22 |
| 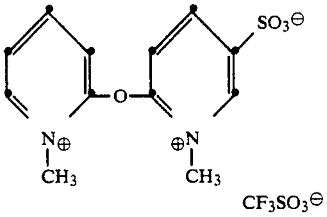 | 23 |
| 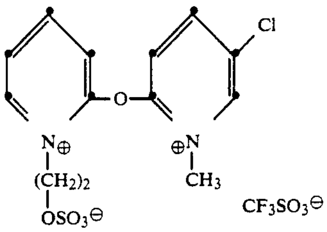 | 24 |
| 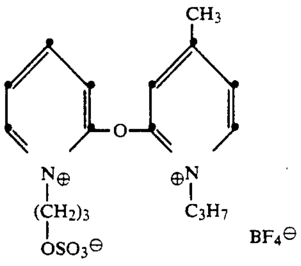 | 25 |
| 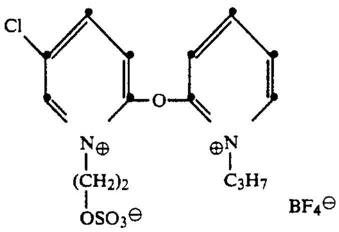 | 26 |
| 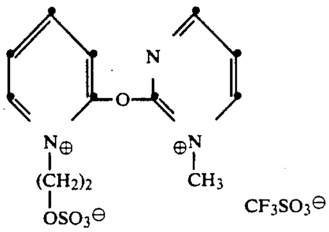 | 27 |

TABLE I-continued

| | Dication Ether Number |
|---|---|
| 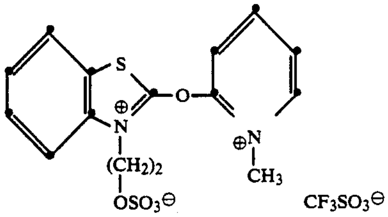 | 28 |
| 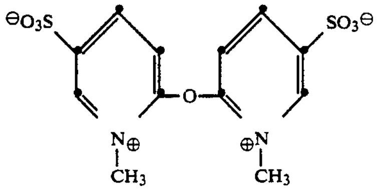 | 29 |
| 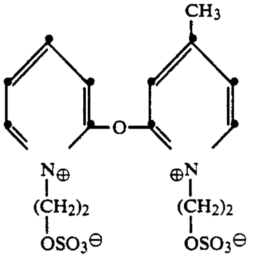 | 30 |
| 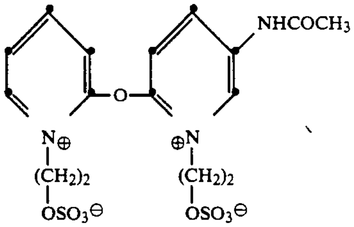 | 31 |
| 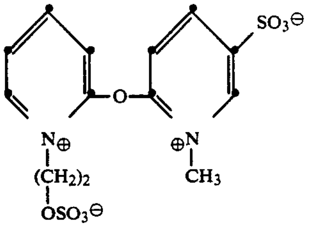 | 32 |
| 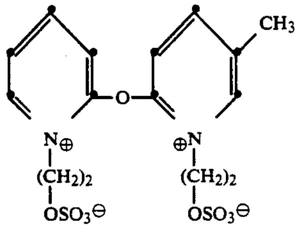 | 33 |
| 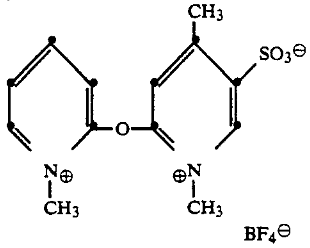 | 34 |
| 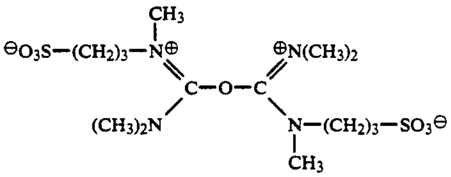 | 35 |
| 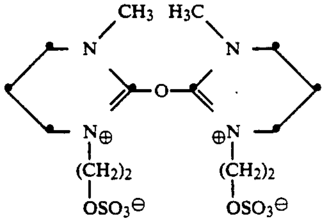 | 36 |
| 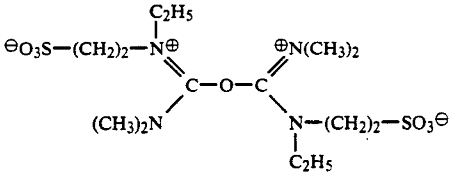 | 37. |

20. The kit of claim 19 wherein the dication ether is selected from ethers 1 and 2 of Table 1 as follows:

TABLE I

| | Dication Ether Number |
|---|---|
| 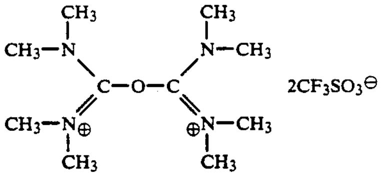 | 1 |
| 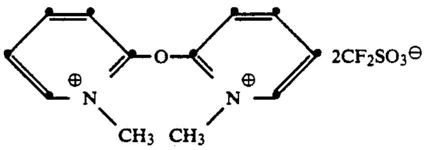 | 2. |

21. The kit of claim 20 wherein the polymer particles are core-shell polymer particles.

22. The kit of claim 20 wherein the polymer particles are about 0.01 to 100 μm in average diameter.

23. The kit of claim 21, 22 or 20 wherein the polymer particles comprise a tracer.

24. The method of claim 1, 11 or 17 wherein the polymer particles are core-shell polymer particles.

25. The method of claim 1, 11 or 17 wherein the polymer particles have an average diameter of 0.01 to 100 μm.

26. The method of claim 1, 11 or 17 wherein the polymer particles comprise a tracer.

* * * * *